(12) United States Patent
Jaiswal et al.

(10) Patent No.: US 8,871,275 B2
(45) Date of Patent: Oct. 28, 2014

(54) EXTENDED RELEASE COMPOSITIONS COMPRISING TOLTERODINE

(75) Inventors: Sunil Beharilal Jaiswal, Nagpur (IN); Ankur Janak Shah, Mumbai (IN)

(73) Assignee: Inventia Healthcare Private Limited (IN)

( * ) Notice: Subject to any disclaimer, the term of this patent is extended or adjusted under 35 U.S.C. 154(b) by 355 days.

(21) Appl. No.: 12/672,435

(22) PCT Filed: Aug. 6, 2008

(86) PCT No.: PCT/IB2008/002135
§ 371 (c)(1),
(2), (4) Date: Feb. 5, 2010

(87) PCT Pub. No.: WO2009/019599
PCT Pub. Date: Feb. 12, 2009

(65) Prior Publication Data
US 2011/0150937 A1    Jun. 23, 2011

(30) Foreign Application Priority Data
Aug. 8, 2007 (IN) .......................... 1534/MUM/2007

(51) Int. Cl.
| A61K 9/16 | (2006.01) |
| A61K 31/137 | (2006.01) |
| A61K 9/14 | (2006.01) |
| A61K 9/20 | (2006.01) |
| A61K 9/22 | (2006.01) |
| A61K 9/48 | (2006.01) |
| A61K 9/52 | (2006.01) |
| A61K 9/54 | (2006.01) |
| A61K 9/56 | (2006.01) |
| A61K 9/60 | (2006.01) |
| A61K 9/62 | (2006.01) |
| A61K 9/50 | (2006.01) |

(52) U.S. Cl.
CPC ............. *A61K 9/5078* (2013.01); *A61K 9/5042* (2013.01); *A61K 9/5047* (2013.01); *A61K 9/5026* (2013.01); *A61K 31/137* (2013.01)
USPC ........... 424/494; 424/489; 424/490; 424/493; 424/495; 424/451; 424/452; 424/457; 424/458; 424/459; 424/461; 424/464; 424/465; 424/468; 514/648; 514/649

(58) Field of Classification Search
None
See application file for complete search history.

(56) References Cited

U.S. PATENT DOCUMENTS

| 5,382,600 A | 1/1995 | Jonsson |
| 5,922,914 A | 7/1999 | Gage |

(Continued)

FOREIGN PATENT DOCUMENTS

| EP | 1 227 806 B1 | 8/2002 |
| EP | 1 629 834 A1 | 3/2006 |

(Continued)

OTHER PUBLICATIONS www.nbent.com; wayback date of Feb. 5, 2005; accessed Nov. 16, 2013; reference describing sodium starch glycolate.*

(Continued)

*Primary Examiner* — Jeffrey T Palenik
(74) *Attorney, Agent, or Firm* — Cook Alex Ltd.

(57) ABSTRACT

The present invention deals with extended release pharmaceutical compositions comprising tolterodine, wherein the composition comprises: a) a drug layer comprising tolterodine tartrate, monosaccharide and/or disaccharide on an inert core; or a drug core comprising tolterodine tartrate, monosaccharide and/or disaccharide; and b) a polymer layer comprising extended release polymer(s). The invention also provides a process for the preparation of the above mentioned composition.

20 Claims, 1 Drawing Sheet

(56) References Cited

U.S. PATENT DOCUMENTS

Figure 1:
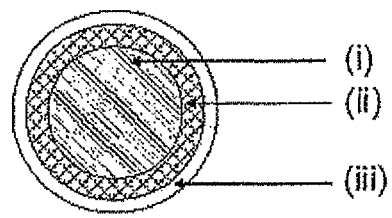
Figure 1:
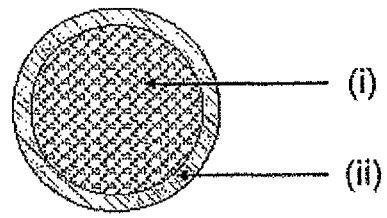

| | | |
|---|---|---|
| 6,310,103 B1 | 10/2001 | Aberg |
| 6,310,248 B2 | 10/2001 | Andersson |
| 6,383,471 B1 | 5/2002 | Chen |
| 6,486,163 B1 | 11/2002 | Leonardi |
| 6,538,035 B2 | 3/2003 | Gillberg |
| 6,566,537 B2 | 5/2003 | Andersson |
| 6,630,162 B1 | 10/2003 | Nilvebrant |
| 6,680,319 B2 | 1/2004 | Leonardi |
| 6,753,011 B2 | 6/2004 | Faour |
| 6,770,295 B1 | 8/2004 | Kreilgard |
| 6,822,119 B1 | 11/2004 | Kumar |
| 6,911,217 B1 | 6/2005 | Gren |
| 7,005,449 B2 | 2/2006 | Hawley |
| 7,101,888 B2 | 9/2006 | Reo |
| 7,138,405 B2 | 11/2006 | Wyllie |
| 7,268,257 B1 | 9/2007 | Yamada |
| 7,335,793 B2 | 2/2008 | Razzeti |
| 7,355,077 B2 | 4/2008 | Venkataraman |
| 7,358,399 B2 | 4/2008 | Turchetta |
| 7,393,874 B2 | 7/2008 | Reddy |
| 7,538,249 B2 | 5/2009 | Kankan |
| 2001/0016669 A1 | 8/2001 | Andersson |
| 2001/0044438 A1 | 11/2001 | Wyllie |
| 2002/0010216 A1 | 1/2002 | Rogosky |
| 2002/0019568 A1 | 2/2002 | Andersson |
| 2002/0132005 A1 | 9/2002 | Faour |
| 2002/0161054 A1 | 10/2002 | Gillberg |
| 2003/0018061 A1 | 1/2003 | Ogawa |
| 2003/0027856 A1 | 2/2003 | Aberg |
| 2003/0050620 A1 | 3/2003 | Odidi |
| 2003/0054041 A1 | 3/2003 | Lemmons |
| 2003/0060513 A1 | 3/2003 | Arneric |
| 2003/0118633 A1 | 6/2003 | Versi |
| 2003/0124179 A1 | 7/2003 | Jacobsen |
| 2003/0152624 A1 | 8/2003 | Aldrich |
| 2003/0180362 A1 | 9/2003 | Park |
| 2003/0185882 A1 | 10/2003 | Vergez |
| 2003/0194420 A1 | 10/2003 | Holl |
| 2003/0199582 A1 | 10/2003 | Hawley |
| 2003/0203899 A1 | 10/2003 | Del Soldato |
| 2004/0047908 A1 | 3/2004 | Lemmons |
| 2004/0067908 A1 | 4/2004 | Nakade |
| 2004/0096499 A1 | 5/2004 | Vaya |
| 2004/0116533 A1 | 6/2004 | Arneric |
| 2004/0137156 A1 | 7/2004 | Lee |
| 2004/0191345 A1 | 9/2004 | Nicklasson |
| 2004/0197397 A1 | 10/2004 | Ebert |
| 2004/0249211 A1 | 12/2004 | Kumar |
| 2005/0008702 A1 | 1/2005 | Raour |
| 2005/0032905 A1 | 2/2005 | Reo |
| 2005/0131067 A1 | 6/2005 | Parthasaradhi |
| 2005/0222165 A1 | 10/2005 | Wyllie |
| 2006/0018933 A1 | 1/2006 | Vaya |
| 2006/0034937 A1 | 2/2006 | Patel |
| 2006/0047007 A1 | 3/2006 | Danehower |
| 2006/0079716 A1 | 4/2006 | Turchetta |
| 2006/0094904 A1 | 5/2006 | Venkataraman |
| 2006/0153916 A1 | 7/2006 | Vaya |
| 2006/0160887 A1 | 7/2006 | Yamagata |
| 2006/0177510 A1 | 8/2006 | Vergez et al. |
| 2006/0189827 A1 | 8/2006 | Razzetti |
| 2006/0194876 A1 | 8/2006 | Kovacs |
| 2006/0194987 A1 | 8/2006 | Kovacs |
| 2006/0263429 A1 | 11/2006 | Feng |
| 2007/0142479 A1 | 6/2007 | Kankan |
| 2007/0149479 A1 | 6/2007 | Fischer |
| 2007/0155838 A1 | 7/2007 | Danehower |
| 2007/0248670 A1 | 10/2007 | van der Heuvel |
| 2008/0050449 A1 | 2/2008 | Arieli |
| 2008/0146844 A1 | 6/2008 | Venkataraman |
| 2008/0188684 A1 | 8/2008 | Martinez |
| 2008/0318982 A1* | 12/2008 | Mastrell et al. ............ 514/262.1 |
| 2009/0017111 A1 | 1/2009 | van de Heuvel |
| 2009/0022797 A1 | 1/2009 | Rossi |
| 2009/0022807 A1 | 1/2009 | Li |
| 2009/0099151 A1 | 4/2009 | Jain |
| 2009/0192228 A1 | 7/2009 | Wang |
| 2009/0208570 A1 | 8/2009 | Mandaogade |
| 2009/0214642 A1 | 8/2009 | Legan |
| 2009/0214665 A1 | 8/2009 | Lai |
| 2009/0311317 A1 | 12/2009 | Cherukuri |

FOREIGN PATENT DOCUMENTS

| | | |
|---|---|---|
| EP | 1 635 795 A1 | 3/2006 |
| EP | 1 652 532 A1 | 5/2006 |
| EP | 1 781 275 | 5/2007 |
| EP | 1 810 668 A1 | 7/2007 |
| EP | 1 839 649 A1 | 10/2007 |
| EP | 1839649 | 10/2007 |
| EP | 1 964 553 A1 | 9/2008 |
| EP | 2 054 372 A2 | 5/2009 |
| WO | WO 9803067 | 1/1998 |
| WO | WO 0027364 | 5/2000 |
| WO | WO 2004012700 A2 | 2/2004 |
| WO | WO 2004019892 A2 | 3/2004 |
| WO | WO 2004105735 A1 | 12/2004 |
| WO | WO 2005048979 A2 | 6/2005 |
| WO | WO 2005065639 A2 | 7/2005 |
| WO | WO 2005079748 A2 | 9/2005 |
| WO | WO2005105036 | 11/2005 |
| WO | WO 2005105036 A1 | 11/2005 |
| WO | WO 2007010509 A2 | 1/2007 |
| WO | WO 2007011131 A1 | 1/2007 |
| WO | WO 2007018943 A2 | 2/2007 |
| WO | WO 2007022255 A2 | 2/2007 |
| WO | WO 2007029087 A2 | 3/2007 |
| WO | WO 2007/072169 * | 6/2007 ........... A61K 31/519 |
| WO | WO 2007082770 A1 | 7/2007 |
| WO | WO 2007141530 A2 | 12/2007 |
| WO | WO 2008012346 A1 | 1/2008 |
| WO | WO 2009057138 A2 | 5/2009 |
| WO | WO 2009080061 A1 | 7/2009 |
| WO | WO 2009121178 A1 | 10/2009 |
| WO | WO 2009135520 A1 | 11/2009 |
| WO | WO 2009140557 | 11/2009 |

OTHER PUBLICATIONS

"Water Structure and Science"; Mary Chaplin; accessed Nov. 16, 2013; last updated Apr. 10, 2012; 5 pg. pdf.*

Supplemental EP Search Report for EP Application No. EP 08789084.4 mailed Jan. 16, 2013.

* cited by examiner

EXTENDED RELEASE COMPOSITIONS COMPRISING TOLTERODINE

This is a national stage application of International Application PCT/IB2008/002135 filed on Aug. 6, 2008, which claims priority to Indian Patent Application 1534/MUM/2007 filed Aug. 8, 2007, both of which are hereby incorporated by reference in their entireties.

FIELD OF THE INVENTION

The present invention relates to extended release pharmaceutical compositions comprising Tolterodine or its salts and a process for preparation thereof.

BACKGROUND OF THE INVENTION

Tolterodine is an anti-muscaranic agent used in the treatment of patients with overactive bladder. Tolterodine Tartrate is currently available as film coated tablets containing 1 mg or 2 mg of the active and also as extended release capsules containing 2 mg or 4 mg of the active. Dry mouth is major side effect associated with tolterodine. To substantially minimize the impact of the side effect, it is desirable to administer tolterodine in extended release dosage form to reduce the frequency of administration and to reduce the frequency of side effects as compared to an immediate release dosage form.

WO0027364, WO03053428, WO0134139 EP1128819, EP1227806, U.S. Pat. No. 6,911,217, U.S. Pat. No. 6,770,295 and U.S. Pat. No. 6,630,102 disclose controlled release beads comprising a core unit of a substantially water soluble or water swellable inert material, a first layer of substantially water insoluble polymer on the core unit, a second layer containing an active ingredient and hydroxypropylmethylcellulose (polymer) as binder covering the first layer and a third layer of polymer on the second layer, wherein the first layer is adapted to control water penetration into the cores. The third layer of polymer is effective for controlled release of the active ingredient.

WO2004/105735, EP1635795, WO2007/029087 disclose a controlled release pharmaceutical composition of tolterodine comprising of one or more coated units, wherein each coated unit comprises a core, a first layer surrounding atleast a portion of the core, the first layer comprising tolterodine and one or more hydrophilic polymers and a second layer surrounding atleast a portion of the first layer and comprising one or more polymers effective for controlled release of the tolterodine from the first layer.

WO2006/021425 and EP1781275 disclose a sustained release composition comprising a core element coated with an outer layer comprising a hydrophobic sustained release polymer. The core element is selected from (i) an inert core with a first layer comprising of tolterodine and a binder and (ii) a matrix core formulation containing a matrix core material, tolterodine and a binder. The binder is preferably selected from polymers such as hydroxypropylmethylcellulose, hydroxypropylcellulose and polyvinylpyrrolidone.

WO2007/122015 discloses a controlled release tolterodine beads comprising a sugar core, an innermost sealcoat layer comprising hydroxypropylmethylcellulose, a drug layer comprising tolterodine and a hydrophilic polymer and an outer control release layer. The thickness of the hydrophilic hydroxypropylmethylcellulose sealcoat layer helps to modulate the release of tolterodine.

EP1839649 discloses a sustained release pharmaceutical composition comprising a) a coat comprising at least one water insoluble permeable polymer and at least one water soluble polymer applied onto b) pellets containing only tolterodine and microcrystalline cellulose (polymer).

It is evident from the prior art that in all formulations, a polymer is necessarily used in combination with the drug. For example:

i) the drug layer containing tolterodine and binder (polymer) is in between the two layers containing water insoluble polymer as in WO0027364, WO03053428, WO0134139, EP1128819, EP1227806, U.S. Pat. No. 6,911,217, U.S. Pat. No. 6,770,295 and U.S. Pat. No. 6,630,102; or ii) the drug layer containing tolterodine and a hydrophilic polymer is in between the innermost sealcoat layer comprising hydroxypropylmethylcellulose and outer control release layer as in WO2007/122016; or iii) the drug layer comprising tolterodine and one or more hydrophilic polymer is coated with one or more polymers as in WO2004/105735, EP1635795 and WO2007/029087; or iv) the drug layer comprising tolterodine and a binder (binder selected from group consisting of cellulose derivative and polyvinyl pyrrolidone, both being polymer) is coated with hydrophobic sustained release polymer as in WO2006/021425 and EP1781275; or v) the drug core containing only tolterodine and microcrystalline cellulose (polymer) is coated with at least one water insoluble permeable polymer and at least one water soluble polymer as in EP1839649.

SUMMARY OF THE INVENTION

The object of the invention is to provide alternate extended release pharmaceutical compositions of tolterodine or its salts so structured as to avoid the use of a combination of drug and polymer in the drug layer or drug core as taught in prior art.

It is another object of the invention to provide extended release pharmaceutical compositions wherein the compositions comprise of an inert core; drug layer comprising of tolterodine or its salts, monosaccharide and/or disaccharide on the inert core; and polymer layer comprising extended release polymer on the drug layer.

It is yet another object of the invention to provide extended release pharmaceutical compositions wherein the composition comprises a drug core of tolterodine or its salts, monosaccharide and/or disaccharide; the drug core being coated with a polymer layer comprising extended release polymer.

It is yet another object of the invention to provide processes for the preparation of the above mentioned compositions.

It is yet another object of the invention to provide the above compositions in the form of pellets capable of being filled in capsules or compressed into tablets.

DETAILED DESCRIPTION OF THE INVENTION

The invention provides alternate extended release pharmaceutical compositions of tolterodine or its salts so structured as to avoid the use of a combination of drug and polymer in the drug layer or drug core as taught in prior art.

The invention provides extended release pharmaceutical compositions comprising tolterodine, wherein the composition comprises of:

a) a drug layer comprising of tolterodine tartrate, monosaccharide and/or disaccharide on an inert core; or a drug core comprising of tolterodine tartrate, monosaccharide and/or disaccharide; and b) a polymer layer comprising of extended release polymer(s).

FIGS. 1(a) and 1(b) illustrate the general structure of the compositions of the present invention.

As shown in FIG. 1(a), the compositions comprise of an inert core (i); the inert core being coated with drug layer (ii) comprising of tolterodine or its salts, monosaccharide and/or disaccharide; the said drug layer being coated with polymer layer (iii) comprising extended release polymer(s).

As shown in FIG. 1(b), the compositions comprise a drug core (i) of tolterodine or its salts, monosaccharide and/or disaccharide; the drug core being coated with polymer layer (ii) comprising extended release polymer(s).

I (a)

A process for the preparation of the extended release pharmaceutical composition comprising tolterodine as shown in FIG. 1 (a) comprises steps of:
- a) providing an inert core comprising of substantially water soluble material or water swellable material or mixtures thereof;
- b) coating the inert core with a drug layer comprising of tolterodine or its salts, monosaccharide and/or disaccharide; and
- c) coating the drug layer with a polymer layer comprising of extended release polymer(s), optionally a plasticizer and optionally anti-tack agent to obtain extended release pellets.

Coating of said inert core with a drug layer comprising steps of:
- a) dispersing and/or dissolving tolterodine or its salts in a solvent selected from water, organic solvent(s), or mixtures thereof to obtain drug dispersion or solution;
- b) dispersing and/or dissolving monosaccharide and/or disaccharide in a solvent selected from water, organic solvent(s), or mixtures thereof;
- c) mixing dispersion or solution of step b) with drug dispersion or solution obtained in step a);
- d) optionally adding anti-tack agent to the dispersion or solution of step c);
- e) spraying the resulting dispersion or solution on the inert core followed by drying and sizing.

Coating of a polymer layer on the drug layer comprising steps of:
- a) dispersing and/or dissolving extended release polymer(s) in a solvent selected from water, organic solvent(s) or mixtures thereof to obtain polymer dispersion or solution;
- b) optionally adding one or more additives selected from anti-tack agent, plasticizer, pigments, colorant, or mixtures thereof to polymer dispersion or solution;
- c) spraying the resulting dispersion or solution on drug layer to obtain extended release pellets;
- d) drying and sizing of extended release pellets.

I (b)

A process for the preparation of the extended release pharmaceutical composition comprising tolterodine as shown in FIG. 1 (b) comprises steps of:
- a) preparing a drug core comprising of tolterodine or its salts, monosaccharide and/or disaccharide, and optionally anti-tack agent;
- b) coating the said drug core with a polymer layer comprising of extended release polymer(s), and optionally a plasticizer or anti-tack agent or mixtures thereof on the drug core to obtain extended release pellets.

Preparation of the said drug core comprises steps of:
- a) mixing tolterodine or its salts, monosaccharide and/or disaccharide and optionally anti-tack agent in a mixer to obtain drug mixture;
- b) granulating the drug mixture with a granulating solvent selected from water, organic solvent(s), or mixtures thereof to obtain granules;
- c) extruding the granules to obtain extrudates;
- d) spheronizing the extrudates to obtain drug core.
- e) drying and sizing the drug core.

Coating of the said drug core with a polymer layer comprising steps of:
- a) dispersing and/or dissolving extended release polymer(s), in a solvent selected from water, organic solvent(s), or mixtures thereof to obtain polymer dispersion or solution;
- b) optionally adding one or more additives selected from anti-tack agent, plasticizer, pigment, colorant, or mixtures thereof to polymer dispersion or solution;
- c) spraying the resulting dispersion or solution on drug core to obtain extended release pellets;
- d) drying and sizing of extended release pellets.

The inert core used in the composition is made of any pharmaceutically acceptable inert excipient selected from water soluble excipient, water swellable excipients or mixtures thereof. The average particle size of inert core is in the range of 150 microns to 1680 microns, preferably between 250 microns to 1190 microns, more preferably between 595 microns to 1000 microns. The inert core is preferably made of material selected from microcrystalline cellulose, sugar, starch, or mixtures thereof.

The term "tolterodine" used in the present invention comprises tolterodine (N,Ndiisopropyl-3-(2-hydroxy-5-methylphenyl)-3-phenylpropanamine), salt of tolterodine, their prodrug, their 5-hydroxmethyl metabolite, including their racemic form, or enantiomeric form. Tolterodine salt is addition salt of tolterodine with an inorganic acid or of organic acid It is preferred to have tolterodine tartrate ((R)—N,Ndi-isopropyl-3-(2-hydroxy-5-methylphenyl)-3-phenylpropanamine L-hydrogen tartrate) as active ingredient.

The composition comprises of tolterodine up to 25% w/w, preferably from 0.01% to 10% w/w, more preferably from 0.1% to 8% w/w and most preferably from 0.5% to 6% w/w of the composition.

Particle size of tolterodine tartrate used is in the range from 0.1 microns to 1000 microns, preferably from 0.5 micron to 500 microns and more preferably from 1 micron to 200 microns.

Monosaccharide and/or disaccharide in the drug layer or in the drug core is at least 10% w/w of the composition, preferably from 12.5 to 97.5% w/w, more preferably from 15% w/w to 90% w/w and most preferably from 20% w/w to 80% w/w of the composition. The monosaccharides and/or disaccharides are selected from glucose, dextrose, fructose, mannitol, sucrose, sorbitol, lactose, galactose, maltose, arabinose, ribose, xylose, erythrose, threose, mannose, or mixtures thereof. The weight ratio of tolterodine to monosaccharide and/or disaccharide in the drug layer or the drug core is from 1:5 to 1:100, preferably from 1:10 to 1:90, more preferably from 1:15 to 1:75, most preferably from 1:20 to 1:50.

Anti-tack agent in the drug layer or the drug core is selected from talc, colloidal silicon dioxide, glyceryl monostearate, sodium lauryl sulfate, glyceryl behenate, stearic acid, magnesium stearate, calcium stearate, or mixtures thereof. The weight ratio of tolterodine to anti-tack agent is generally in the range of 1:0.1 to 1:20, preferably in the ratio of 1:0.5 to 1:10, more preferably in the range of 1:1 to 1:5 and most preferably in the range of 1:1.5 to 1:2.5.

The extended release polymer in the polymer layer is selected from at least one water insoluble polymer or a mixture of at least one water insoluble polymer with at least one water soluble polymer.

Extended release polymer is up to 30% w/w of the composition, preferably from 1% w/w to 15% w/w of the composition, more preferably from 1% w/w to 10% w/w of the composition, most preferably from 3% w/w to 8% w/w of the composition.

Such polymers are selected from the group of cellulose derivatives, acrylic acid derivatives, polymethacrylate(s), starch, polyvinyl alcohol, polyvinyl acetate, povidone, polyalkylene glycol such as polyethylene glycol, cellulose esters such as cellulose acetate, or mixtures thereof.

Cellulose derivative is selected from ethylcellulose, hydroxypropylcellulose, microcrystalline cellulose, hydroxypropylmethylcellulose, hydroxyethylcellulose, methylcellulose, sodium carboxymethylcellulose, cellulose acetate phthalate, hydroxypropylmethylcellulose phthalate, hydroxypropylmethylcellulose acetate succinate, cellulose acetate butyrate, cellulose acetate trimellitate, or mixtures thereof. Ethylcellulose is available as a dry powder (Ethocel® of Dow, U.S.A.) or as aqueous dispersion marketed under the trade name Aquacoat® of FMC, USA or Surelease® of Colorcon, USA, Ethylcellulose of various available viscosities grades ranging from 3 mpas to 50 mpas can be used.

Polymethacrylate is selected form poly(ethyl acrylate, methylmethacrylate) 2:1 marketed under the trade name of Eudragit® NE30D of Rohm Pharma, Germany, Poly(ethyl acrylate methylmethacrylate, trimethylammonioethyl methacrylate chloride) 1:2:0.2 marketed under the trade name of Eudragit® RL of Rohm Pharma, Germany, Poly(ethylacrylate methylmethacrylate, trimethylammonioethyl methacrylate chloride) 1:2:0.1 marketed under the trade name of Eudragit® RS of Rohm Pharma, Germany, Poly(methacrylic acid, methyl methacrylate) 1:1 marketed under the trade name of Eudragit® L of Rohm Pharma, Germany, Poly (methacrylic acid, ethyl acrylate) 1:1 marketed under the trade name of Eudragit® L 30D-55 and Eudragit® L100-55 of Rohm Pharma, Germany, Poly(methacrylic acid, methyl methacrylate) 1:2 marketed under the trade name of Eudragit® S of Rohm Pharma, Germany.

The polymer layer comprising extended release polymer optionally comprises one or more additives selected from anti-tack agent, plasticizer, pigment, colorant, or mixtures thereof.

Plasticizer in the polymer layer is up to 30% w/w, preferably from 1% w/w to 20% w/w, more preferably from 5% w/w to 15% w/w and most preferably from 7.5% w/w to 12.5% w/w of the polymer layer. Plasticizer is selected from the group of hydrophilic and hydrophobic plasticizer preferably selected from triacetin, triethylcitrate, polyethylene glycol, acetyltribytylcitrate, miglyol, hydrogenated oils, propylene glycol, acetyltriethylcitrate, polysorbate, cetyl alcohol, oleic acid, propylene glycol, dibutylsebacate, diethylphthalate, dibutylphthalate, meglumine, or mixtures thereof.

Anti-tack agent in the polymer layer is up to 30% w/w, preferably from 1% w/w to 20% w/w, more preferably from 5% w/w to 15% w/w and most preferably from 7.5% w/w to 12.5% w/w of the polymer layer. Anti-tack agent is selected from talc, colloidal silicon dioxide, glyceryl monostearate, sodium lauryl sulfate, waxes, glyceryl behenate, stearic acid, magnesium stearate, calcium stearate, or mixtures thereof.

Colors, pigments and dyes are selected from pharmaceutically acceptable colors, pigments and dyes and preferably selected from titanium dioxide and iron oxide.

The solvent is selected from water, organic solvent(s), or mixtures thereof. The organic solvent(s) is selected from alcohol, dichloromethane, acetone, halogenated hydrocarbon, ethylmethylketone, or mixtures thereof.

Alcohol is selected from methanol, ethanol, isopropanol, or mixtures thereof.

Any equipment, suitable for the preparation of extended release pellets comprising tolterodine may be utilized. The preferred equipments are selected from coating pan, fluid bed processor preferably bottom spray, CF coater, extruder spheronizer and the likes. The process may be carried out in single equipment or in a combination of two or more equipments.

Extended release compositions comprising tolterodine tartrate when analyzed in-vitro in USP apparatus, type I basket in pH 6.8 phosphate buffer exhibited the in-vitro dissolution profile of:
not less than 5% of tolterodine tartrate after 1 hour;
not less than 15% of tolterodine tartrate after 2 hours;
not less than 30% of tolterodine tartrate after 4 hours; and
not less than 70% of tolterodine tartrate after 12 hours.

Preferably, the extended release compositions comprising tolterodine tartrate exhibited the in-vitro dissolution profile of:
5% to 45% of tolterodine tartrate after 1 hour;
15% to 60% of tolterodine tartrate after 2 hours;
30% to 80% of tolterodine tartrate after 4 hours; and
70% to 100% of tolterodine tartrate after 12 hours The release rate of tolterodine tartrate from the dosage form increases with decreasing quantity of extended release polymer and decreases with increasing quantity of extended release polymer.

Extended release pellets comprising tolterodine tartrate complying with the desired dissolution profile are filled in capsule or compressed into tablets using the process known in the art to deliver the therapeutic dose of tolterodine tartrate.

The invention further provides non-limiting examples.

Example 1

8 g of tolterodine tartrate was dissolved in purified water to obtain drug solution. 160 g of sucrose was dissolved in purified water to obtain sucrose solution. Drug solution was added to sucrose solution. 2 g of talc and 2 g of colloidal silicon dioxide was added to the resulting solution to obtain drug dispersion. The resulting dispersion was sprayed on 268 g of inert cores in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain drug layer coated inert cores. The drug layer coated inert cores so obtained were dried in fluid bed bottom spray processor to have moisture content of less than 5%, preferably less than 3% and more preferably less than 2% w/w.

14.08 g of ethylcellulose (10 mpas) and 3.52 g of hydroxypropylmethylcellulose were dispersed and dissolved in the mixture of methanol and dichloromethane. The resulting solution was sprayed on drug core in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets. These extended release pellets so obtained were dried in fluid bed bottom spray processor to have moisture content of less than 5%, preferably less than 3% and more preferably less than 2% w/w.

Example 2

8.4 g of tolterodine tartrate was mixed with 168 g of lactose monohydrate and 42 g dextrose monohydrate to obtain drug mixture. Drug mixture was granulated with purified water to obtain the granules. The granules were extruded to obtain extrudates. These extrudates were spheronized to obtain drug core. The drug cores were dried and sized.

4.86 g of ethylcellulose (10 mpas) and 0.49 g of triacetin were dissolved in the mixture of methanol and dichloromethane. The resulting solution was sprayed on drug cores in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets. These extended release pellets so obtained were dried in fluid bed bottom spray processor to have moisture content of less than 5%, preferably less than 3% and more preferably less than 2% w/w.

The extended release pellets comprising tolterodine tartrate as prepared in examples 1-2 were filled in different sized capsules or compressed into tablets to deliver the dose of 2 mg and 4 mg.

Extended release pellets or capsules comprising tolterodine tartrate as prepared in examples 1 to 2 when analyzed in-vitro in USP apparatus, type I basket in pH 6.8 phosphate buffer exhibited in-vitro dissolution profile in the range of about:
10%-20% of tolterodine tartrate after 1 hour;
18%-40% of tolterodine tartrate after 2 hours;
33%-60% of tolterodine tartrate after 4 hours; and
75%-80% of tolterodine tartrate after 12 hours.

Example 3

4 g of tolterodine tartrate was dissolved in methanol to obtain drug solution. 40 g of sucrose was dissolved in purified water to obtain sucrose solution. Drug solution was mixed with sucrose solution. 8 g of colloidal silicon dioxide was added to the resulting solution to obtain drug dispersion. The resulting dispersion was sprayed on 128 g of inert core in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain drug layer coated inert core. The drug layer coated inert cores so obtained were dried in fluid bed bottom spray processor to have moisture content of less than 5%, preferably less than 3% and more preferably less than 2% w/w.

9.72 g of ethylcellulose (10 mpas), 1.78 g of hydroxypropylmethylcellulosephthalate HP 55 and 3.08 g of hydroxypropylmethylcellulose E05 were dispersed and dissolved in the mixture of isopropanol and dichloromethane. 1.62 g of triethylcitrate was added and the resulting solution was sprayed on drug layer coated inert cores in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets. These extended release pellets so obtained were dried in fluid bed bottom spray processor to have moisture content of less than 5%, preferably less than 3% and more preferably less than 2% w/w.

Example 4

Drug layer coated inert cores were prepared as described in example 3.

9.36 g of ethylcellulose (10 mpas) and 3.6 g of hydroxypropylmethylcellulose E05 were dispersed and dissolved in the mixture of isopropanol and purified water. 1.44 g of triethylcitrate was added and the resulting solution was sprayed on drug layer coated inert cores in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets. These extended release pellets so obtained were dried in fluid bed bottom spray processor to have moisture content of less than 5%, preferably less than 3% and more preferably less than 2% w/w.

Example 5

Drug layer coated inert cores were prepared as described in example 3.

12.21 g of ethylcellulose (10 mpas), 3.05 g of hydroxypropylmethylcellulosephthalate HP 55 and 3.05 g of hydroxypropylmethylcellulose E06 were dispersed and dissolved in the mixture of isopropanol dichloromethane and purified water. 2.03 g of dibutylsebacate was added and the resulting solution was sprayed on drug layer coated inert cores in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets. These extended release pellets so obtained were dried in fluid bed bottom spray processor to have moisture content of less than 5%, preferably less than 3% and more preferably less than 2% w/w.

The extended release pellets comprising tolterodine tartrate as prepared in examples 3-5 were filled in different sized capsules or compressed into tablets to deliver the dose of 2 mg and 4 mg.

These extended release pellets or capsules when analyzed in-vitro in USP apparatus, type I basket in pH 6.8 phosphate buffer exhibited dissolution profile in the range of about:
12%-20% of tolterodine tartrate after 1 hour;
38%-48% of tolterodine tartrate after 2 hours;
68%-75% of tolterodine tartrate after 4 hours; and
90%-100% of tolterodine tartrate after 12 hours.

The release rate of tolterodine tartrate from the dosage form increases with decreasing quantity of extended release polymer and decreases with increasing quantity of extended release polymer.

We claim:
1. An extended release pharmaceutical composition comprising tolterodine and an extended release polymer(s), wherein the composition comprises:
  a) i) a drug layer comprising tolterodine tartrate and monosaccharide and/or disaccharide on an inert core wherein the drug layer is substantially free of the extended release polymer; or
    ii) a drug core comprising tolterodine tartrate and monosaccharide and/or disaccharide wherein the drug core is substantially free of the extended release polymer; and b) a polymer layer comprising extended release polymer(s).

2. The composition of claim 1, wherein tolterodine tartrate is 0.1 to 8% w/w of the composition.

3. The composition of claim 1, wherein the monosaccharide and/or disaccharide in the drug layer or the drug core is selected from glucose, dextrose, fructose, mannitol, sucrose, sorbitol, lactose, galactose, maltose, arabinose, ribose, xylose, erythrose, threose, mannose, or mixtures thereof.

4. The composition of claim 1, wherein the monosaccharide and/or disaccharide in the drug layer or the drug core is at least 10% w/w of the composition.

5. The composition of claim 1, wherein the weight ratio of tolterodine tartrate to monosaccharide and/or disaccharide in the drug layer or the drug core is from 1:5 to 1:100.

6. The composition of claim 1, wherein the drug layer or the drug core further comprises of anti-tack agent selected from talc, colloidal silicon dioxide, glyceryl monostearate, sodium lauryl sulfate, glyceryl behenate, stearic acid, magnesium stearate, calcium stearate, or mixtures thereof.

7. The composition of claim 6, wherein weight ratio of tolterodine to anti-tack agent in the drug layer or the drug core is from 1:0.1 to 1:20.

8. The composition of claim 1, wherein the extended release polymer is selected from ethylcellulose, polymethacrylate(s), cellulose acetate phthalate, hydroxypropylmethylcellulose phthalate, hydroxypropylmethylcellulose acetate succinate, cellulose acetate butyrate, cellulose acetate trimellitate, cellulose acetate, hydroxypropylcellulose, povidone, polyvinyl alcohol, polyvinyl acetate, polyethylene glycol, hydroxypropylmethylcellulose, starch, hydroxyethylcellulose, microcrystalline cellulose, sodium carboxymethylcellulose, methylcellulose, or mixtures thereof.

9. The composition of claim 1, wherein the polymer layer further comprises of plasticizer selected from triacetin, triethylcitrate, polyethylene glycol, acetyltribytylcitrate, miglyol, hydrogenated oils, acetyltriethylcitrate, polysorbate, oleic acid, cetyl alcohol, propylene glycol, dibutylsebacate, diethylphthalate, dibutylphthalate, meglumine, or mixtures thereof.

10. A process for the preparation of an extended release pharmaceutical composition comprising tolterodine, wherein the process comprises the steps of:
a) providing an inert core comprising a substantially water soluble material, a water swellable material, or mixtures thereof;
b) coating the inert core with a drug layer comprising tolterodine tartrate, and monosaccharide and/or disaccharide; and
c) coating the drug layer with a polymer layer comprising extended release polymer(s), optionally a plasticizer and optionally an anti-tack agent to obtain extended release pellets, wherein the drug layer is substantially free of the extended release polymer(s).

11. The process of claim 10, wherein the coating of drug layer on the inert core comprising steps of:
a) dispersing and/or dissolving tolterodine tartrate in a solvent selected from water, organic solvent(s), or mixtures thereof to obtain drug dispersion or solution;
b) dispersing and/or dissolving monosaccharide and/or disaccharide in a solvent selected from water, organic solvent(s), or mixtures thereof;
c) mixing dispersion or solution of step b) with drug dispersion or solution obtained in step a);
d) optionally adding anti-tack agent to the dispersion or solution of step c); and
e) spraying the resulting dispersion or solution on the inert core followed by drying and sizing.

12. A process for the preparation of an extended release pharmaceutical composition comprising tolterodine, wherein the process comprises the steps of:
a) preparing a drug core comprising tolterodine tartrate, monosaccharide and/or disaccharide, and optionally an anti-tack agent; and
b) coating said drug core with a polymer layer comprising extended release polymer(s), and, optionally, a plasticizer, an anti-tack agent or mixtures thereof, on the drug core to obtain extended release pellets, wherein the drug core is substantially free of the extended release polymer(s).

13. The process of claim 12, wherein preparation of the drug core comprises steps of:
a) mixing tolterodine tartrate, monosaccharide and/or disaccharide and optionally anti-tack agent in a mixer to obtain drug mixture;
b) granulating the drug mixture with a granulating solvent selected from water, organic solvent(s), or mixtures thereof to obtain granules;
c) extruding the granules to obtain extrudates; and
d) spheronizing the extrudates to obtain drug core; and
e) drying and sizing the drug core.

14. The process of claim 10 or 12, wherein coating of the extended release polymer(s) onto the drug layer or onto the drug core comprises the steps of:
a) dispersing and/or dissolving extended release polymer(s) in a solvent selected from water, organic solvent (s) or mixtures thereof to obtain polymer dispersion or solution;
b) optionally adding one or more additives selected from anti-tack agent, plasticizer, pigments, colorant, or mixtures thereof to polymer dispersion or solution;
c) spraying the resulting dispersion or solution on drug layer to obtain extended release pellets; and
d) drying and sizing of extended release pellets.

15. The process of claim 10 or 12, wherein tolterodine tartrate is from 0.1% to 8% w/w of the composition.

16. The process of claim 10 or 12, wherein the monosaccharide and/or disaccharide is selected from glucose, dextrose, fructose, mannitol, sucrose, sorbitol, lactose, galactose, maltose, arabinose, ribose, xylose, erythrose, threose, mannose and mixtures thereof.

17. The process of claim 10 or 12, wherein the monosaccharide and/or disaccharide is at least 10% w/w of the composition.

18. The process of claim 10 or 12, wherein the weight ratio of tolterodine tartrate to monosaccharide and/or disaccharide in the drug layer or the drug core is from 1:5 to 1:100.

19. The process of claim 10 or 12, wherein the weight ratio of tolterodine tartrate to anti-tack agent in the drug layer or drug core is from 1:0.1 to 1:20.

20. The process of claim 10 or 12, wherein the extended release polymer is selected from ethylcellulose, polymethacrylate(s), cellulose acetate phthalate, hydroxypropylmethylcellulose phthalate, hydroxypropylmethylcellulose acetate succinate, cellulose acetate butyrate, cellulose acetate trimellitate, cellulose acetate, hydroxypropylcellulose, povidone, polyvinyl alcohol, polyvinyl acetate, polyethylene glycol, microcrystalline cellulose, hydroxypropylmethylcellulose, hydroxyethylcellulose, starch, sodium carboxymethylcellulose, methylcellulose, or mixtures thereof.

* * * * *